(12) United States Patent
Clark et al.

(10) Patent No.: US 6,274,770 B1
(45) Date of Patent: Aug. 14, 2001

(54) PROCESS FOR PREPARATION OF AROMATIC COMPOUNDS

(75) Inventors: James Hanley Clark, York; David Adams, Beeston Leeds, both of (GB)

(73) Assignee: Victrex Manufacturing Limited, Thornton (GB)

( * ) Notice: Subject to any disclaimer, the term of this patent is extended or adjusted under 35 U.S.C. 154(b) by 0 days.

(21) Appl. No.: 09/380,598

(22) PCT Filed: Mar. 12, 1998

(86) PCT No.: PCT/GB98/00622
§ 371 Date: Sep. 13, 1999
§ 102(e) Date: Sep. 13, 1999

(87) PCT Pub. No.: WO98/40338
PCT Pub. Date: Sep. 17, 1998

(30) Foreign Application Priority Data

Mar. 13, 1997 (GB) .................................................. 9705159

(51) Int. Cl.$^7$ .................................................. C07C 45/25
(52) U.S. Cl. ............................................. 568/323; 568/309
(58) Field of Search .................... 568/309, 321, 568/332, 323, 316; 570/143, 147, 199, 206, 260, 261

(56) References Cited

U.S. PATENT DOCUMENTS 4,263,458 * 4/1981 Bowden et al. ..................... 568/323

FOREIGN PATENT DOCUMENTS 0 004 710   10/1979  (EP) .

OTHER PUBLICATIONS

Database WPI, Section Ch, Week 8637, Derwent Publications Ltd., London, GB; Class E14, An 86–242903 & JP 61 172 845 A, (1986).

J. Chem. Research (S), 1994, pp. 102–103, "Catalytic Oxidation of Diphenylmethanes using Aluminasupported fluorides".

J. Chem. Research (S), 1994, pp. 478–479, "Aromatic Fluorodenitrations using Tetramethylammonium Fluoride".

* cited by examiner

Primary Examiner—Sreeni Padmanabhan
(74) Attorney, Agent, or Firm—Arent Fox Kintner Plotkin Kahn PLLC

(57) ABSTRACT

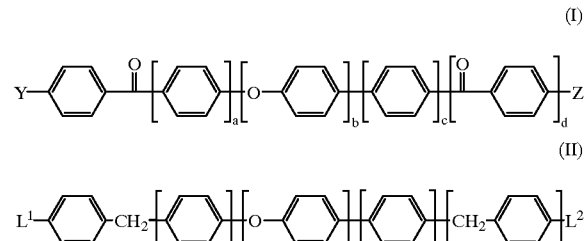

There is disclosed a process for the preparation of a compound of general formula (I), wherein Y and Z each independently represent a fluorine atom or a hydroxy group, and a, b, c and d independently represent 0, 1, 2 or 3 provided that the sum of a, b, c, and d is 1, 2, 3 or 4; the process comprising treating a compound of general formula (II), wherein a, b, c, and d are as described above and $L^1$ and $L^2$ each independently represent an active group provided that either Y and $L^1$ are different or Z and $L^2$ are different, with a fluorinating system in the presence of oxygen. A preferred compound of general formula (I) is 4,4'-difluorobenzophenone which may be prepared from 4,4'-dinitrophenylmethane using tetramethylammonium fluoride.

11 Claims, No Drawings

PROCESS FOR PREPARATION OF AROMATIC COMPOUNDS

This is a U.S. National stage Application of PCT/GB98/00622 filed Mar. 12, 1998.

This invention relates to the preparation of aromatic compounds and particularly, although not exclusively, relates to the preparation of substituted benzophenone compounds, for example, 4,4'-difluorobenzophenone. 4,4'-difluorobenzophenone is an important monomeric reagent used in the production of polyketones, notably polyetheretherketone (PEEK), for example as described in EP 001 879 (Imperial Chemical Industries).

Numerous processes have been proposed for the preparation of 4,4'-difluorobenzophenone. Many known processes use fluorobenzene as a starting material. For example, JP 8961870 (Ihara) and EP 307320 (Raychem) disclose reactions which involve Friedel Crafts acylation of fluorobenzene using 4-fluorobenzoyl chloride in the presence of a catalyst. FR 2647108 (Rhone-Poulenc) discloses acylation of fluorobenzene using benzoic acid in the presence of a catalyst. Two other processes which use fluorobenzene as a starting material are described in JP 61221146 (Asahi) and EP 402623 (Rhone-Poulenc). The former process involves the reaction of fluorobenzene with carbon monoxide in the presence of oxygen and the latter process involves the reaction of fluorobenzene with phosgene to produce the desired product. One problem associated with the use of fluorobenzene is its cost. In addition, the handling and disposal of large amounts of spent catalyst used in the various processes is costly. Furthermore, some of the processes described produce relatively low yields of 4,4'-difluorobenzophenone.

Another known process is described in EP 0 004 710 (Imperial Chemical Industries) and this involves the reaction of 4,4'-diaminodiphenylmethane with an aqueous solution of sodium nitrite and hydrogen fluoride to produce 4,4'-difluorodiphenylmethane which may then be oxidised using nitric acid to produce 4,4'-difluorobenzophenone. Problems associated with this process include the corrosiveness of hydrogen fluoride and undesirable nitrogen oxide biproducts of the reaction.

Other known processes involve the oxidation of 4,4'-difluorodiphenylmethane in the presence of a catalyst, for example a cerium (IV) compound as described in JP 1172845 (Asahi) or a cobalt compound as described in JP 61183245 (Ashai). One problem associated with each of these processes is the need to dispose of the catalyst.

It is an object of the present invention to address problems associated with known processes for the preparation of substituted benzophenone compounds, for example 4,4'-difluorobenzophenone.

The invention is based on the discovery that a fluorination system can be used in both the oxidation and functionalisation of diphenylmethane derivatives for preparing substituted benzophenone compounds.

According to the invention, there is provided a process for the preparation of a compound of general formula (I)

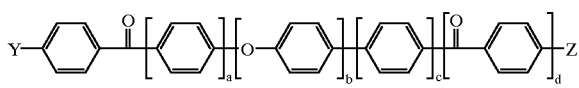

wherein Y and Z each independently represent a fluorine atom or a hydroxy group, and a, b, c and d independently represent 0, 1, 2 or 3 provided that the sum of a, b, c and d is 1, 2, 3 or 4, the process comprising treating a compound of general formula (II)

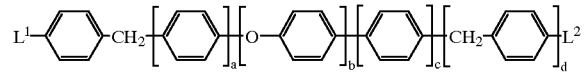

wherein a, b, c and d are as described above and $L^1$ and $L^2$ each independently represent an active group provided that either Y and $L^1$ are different or Z and $L^2$ are different, with a fluorinating system in the presence of oxygen.

Unless otherwise stated in this specification, an alkyl group may have up to 10, suitably up to 8, preferably up to 6, more preferably up to 4, carbon atoms, with methyl and ethyl groups being especially preferred. Additionally, unless otherwise stated, an aryl group may be a benzyl or phenyl group, with a phenyl group being especially preferred.

Said active group is suitably a group which is not inert and can, therefore, be involved in a subsequent reaction, for example as a bridging group or a leaving group. $L^1$ and $L^2$ may be independently selected from halogen atoms, especially fluorine, chlorine and. bromine atoms, or nitro, amino, alkoxy or hydroxy groups. Said fluorinating system is preferably involved in the subsequent reaction of one or each active group.

Preferably, $L^1$ and $L^2$ each independently represent a leaving group or a group which is oxidisable to a leaving group. Leaving groups $L^1$ and $L^2$ are preferably arranged to be displaced in a nucleophilic substitution reaction involving said fluorinating system. Preferably, $L^1$ and $L^2$ each independently represent a halogen, especially a chlorine atom, or a nitro or amino group. More preferably, $L^1$ and $L^2$ each independently represent a nitro group.

$L^1$ and $L^2$ may be the same or different. Preferably, $L^1$ and $L^2$ represent the same atom or group. Preferably, Y and $L^1$ represent different atoms or groups and Z and $L^2$ represent different atoms or groups.

Preferably, a, b, c and d independently represent 0, 1 or 2. More preferably, a, b, c and d independently represent 0 or 1.

Preferably, the sum of a, b, c and d is 1, 2 or 3, and is more preferably 1 or 2. Especially preferred is the case wherein the sum is 1.

Preferably, a represents 0 or 1, more preferably 1. b may represent 0, 1 or 2 and preferably represents 0 or 1, more preferably 0.

Preferably, c represents 0 or 1, more preferably 0. Preferably, d represents 0 or 1, more preferably 0.

Preferred compounds of general formuli I and II are selected from compounds wherein a=1, b=0, c=0, d=0; a=1, b=0, c=0, d=1; a=1, b=0, c=1, d=1; a=1, b=1, c=0, d=1; a=1, b=2, c=0, d=1; and a=1, b=1, c=0, d=0. Most preferably, a=1, b=0, c=0, d=0.

Preferably, said compound of general formula II represents 4,4'-diaminodiphenylmethane or 4,4'-dinitrodiphenylmethane. More preferably, said compound of general formula II represents 4,4'-dinitrodiphenylmethane.

Compounds of general formula II may be commercially available or may be prepared using standard techniques. For example, the compounds may be prepared by reacting a 4-substituted (chloromethyl)benzene derivative, for example 4-nitro(chloromethyl)benzene, with a suitable benzene derivative in a Friedel Crafts reaction.

Said fluorinating system is preferably involved in the oxidation of the or each group —$CH_2$— in said compound of general formula II. For example, said fluorinating system may catalyse the oxidation reaction. Preferably, said fluorinating system acts as a base in the oxidation reaction. It is believed that the fluorinating system, for example a fluoride ion thereof, may deprotonate the or each group —$CH_2$—.

Said fluorination system is preferably involved in both the oxidation of the or each group —$CH_2$— and in the reaction, for example the displacement, of the group $L^1$ and/or group $L^2$. For example, where group $L^1$ and/or group $L^2$ represent a nitro group, said fluorinating system is preferably capable of fluorodenitrating each nitro group.

Preferably, the oxidation of the or each group —$CH_2$— and the reaction of group $L^1$ and/or group $L^2$ occur in the same reaction mixture and/or in the same vessel suitably without the need for the product of one step to be isolated or otherwise separated from the reaction mixture prior to a second step. It is believed that the first step comprises the oxidation of the or each group —$CH_2$— and the second step comprises reaction of group $L^1$ and/or group $L^2$.

Said fluorinating system may include an organics soluble fluoride source and compounds for the preparation of the aforesaid in situ; and alkali metal fluorides, suitably in conjunction with a catalyst. Preferably, said fluorinating system includes one or more compounds selected from only one class of reagents, wherein one class comprises an organics soluble fluoride source as described herein and another class comprises alkali metal fluorides as described herein. The fluorinating system preferably includes only one compound from one class of reagents described herein.

Preferably, said organics soluble fluoride source comprises an onium fluoride derivative. Said onium fluoride derivative may be selected from ammonium, phosphonium and sulphonium fluoride derivatives, with ammonium and phosphonium derivatives being preferred and ammonium derivatives being especially preferred. Preferably, said onium fluoride derivative includes alkyl or aryl groups or mixed alkyl and/or aryl groups. Where the onium fluoride derivative is an ammonium or phosphonium fluoride derivative, it may comprise a cation of general formula $[QR^1_x R^2_y]^+$ wherein Q represents a nitrogen or phosphorous atom, each $R^1$ independently represents an optionally substituted alkyl group, each $R^2$ independently represents an optionally substituted alkyl or aryl group and x and y independently represent 0, 1, 2, 3 or 4 provided that x+y=4. Preferably, each $R^1$ independently represents a $C_{1-20}$ alkyl group and each $R^2$ independently represents a $C_{1-20}$ alkyl group or a benzyl or a phenyl group. Preferably, $R^1$ and/or $R^2$ are unsubstituted. Said onium fluoride derivative may be a fluoride material of general formula $QR^1_x R^2_y F(HF)_z$ where Q, $R^1$, $R^2$, X and y are as described above and z represents 0 to 3, preferably 0 or 1. Suitable ammonium fluoride derivatives are tetraalkyl derivatives with $(CH_3)_4NF$, $(C_2H_5)_4 NF$, $(n—C_4H_9)_4NF$ and $(CH_3)_4NF(HF)$ being preferred. Of the aforesaid, $(CH_3)_4NF$ and $(CH_3)_4NF(HF)$ are especially preferred. A mixed alkyl derivative may be cetyldimethylethylammonium fluoride. Preferred phosphonium fluoride derivatives are tetraphenyl derivatives, with $(C_6H_5)_4PHF_2$ being especially preferred.

Preparation of the ammonium or phosphonium fluoride derivatives may be accomplished using standard procedures. For example, tetramethylammonium fluoride may be prepared in situ by reaction of tetramethylammonium chloride with potassium fluoride, optionally in the presence of a phase transfer catalyst, for example as described in J.Org.Chem 1989,54,4827. Many ammonium or phosphonium fluoride derivatives are commercially available.

Preparation of sulphonium fluoride derivatives may be accomplished using standard procedures. For example, tris (dimethylamino)sulphonium bifluoride can be prepared by treating tris(dimethylamino)sulphonium difluorotrimethylsilicate with water in acetonitrile.

In some cases, onium fluoride derivatives of the type described herein may be supported to provide an ion exchange resin. For example, an onium fluoride derivative such as the group —$CH_2N^+(CH_3)_3F^-$ may be bonded to the 4-position of a cross-linked polystyrene matrix to provide an ion exchange resin.

Preferred alkali metal fluorides include potassium fluoride and caesium fluoride. Suitable catalysts include phase transfer catalysts, for example $(C_6H_5)_4PBr$ and 18-crown-6. Alternatively, alkali metal fluorides may be supported. Suitable supported reagents include $KF^-$ on $CaF_2$ and KF on alumina.

Preferably, an alkali metal fluoride fluorinating system is selected from KF, KF/$(C_6H_5)_4PBr$ (phase transfer catalyst), KF/18-crown-6 (phase transfer catalyst), CsF, KF/CsF, KF-$CaF_2$ (supported reagent), CsF-$CaF_2$ (supported reagent), KF/tetramethylammonium fluoride and KF/tetramethylammonium chloride.

Preferably, said fluorinating system includes ammonium or phosphonium fluoride derivatives of the type described above, with organics soluble derivatives being especially preferred.

Said oxygen is involved in the oxidation of the or each —$CH_2$— group of said compound of general formula II. Said oxygen suitably refers to free oxygen gas which is arranged to contact the reactants in the process and react with said compound of general formula II. Said oxygen gas may be a component of air which contacts the reaction mixture or may be a component of another gaseous mixture which contacts the reaction mixture. In some circumstances, substantially pure oxygen gas may be used. In the process, a gas comprising or consisting essentially of oxygen may be directed into the reaction mixture. Conveniently, an air stream may be blown into the reaction mixture.

Said process is preferably carried out in the presence of a solvent. Said solvent is preferably aprotic. Said solvent is preferably non-aqueous. Said solvent is preferably substantially free of water, at least at the beginning of the process. The solvent may be polar or non-polar. It is preferably polar and adapted to stabilise intermediates formed during the process. Said solvent may be selected from cyanide compounds, especially alkylcyanide compounds; ethers, including cyclic ethers; solvents having —S=O moieties, for example sulphone or sulphoxide solvents; and amides, including cyclic amides.

A preferred alkyl cyanide compound is acetonitrile. A preferred ether is tetrahydrofuran. Solvents having —S=O moieties include alkyl and/or aryl (including alkyl/aryl) sulphones and sulphoxides including cyclic compounds. Preferred amides may be aliphatic or cyclic. Preferred solvents include acetonitrile, tetrahydrofuran, ethers, dimethylsulphoxide, dimethylacetamide, dimethyl formamide, N-methylpyrrolidone, sulpholane, diphenylsulphone and diphenylsulphoxide. Especially preferred solvents are solvents having —S=O moieties and amides as described.

The process may be carried out in a mixture of solvents which mixture includes one or more of the aforementioned solvents.

Preferred solvents have a boiling point of at least 120° C., preferably at least 140° C., more preferably at least 160° C. Said boiling point may be less than 500° C., preferably less than 400° C., more preferably less than 300° C.

The process is preferably carried out above ambient temperature. The process may be carried out at a temperature of greater than 50° C., preferably of greater than 65° C. and, more preferably, of greater than 80° C.

In the process, water is preferably initially removed from the fluorinating system by suitable means. For example, a fluorinating system, such as an ammonium or phosphonium fluoride derivative in a solvent, such as dimethylsulphoxide may be azeotropically dried by adding a hydrocarbon solvent such as cyclohexane in large excess to the fluorinating system and heating at an elevated temperature for several hours under an inert atmosphere such as argon so that water is driven off (see D Wails, D. Phil. Thesis, University of York, England, 1994). Other drying techniques may also be used. A preferred technique involves the use of a vacuum, suitably at an elevated temperature. After drying, the argon atmosphere may be replaced with an atmosphere containing oxygen by providing an air feed. The temperature of the reaction mixture may be raised, for example to about 100° C. and a compound of general formula II added. Heating of the reaction mixture may continue for more than 10 hours, preferably more than 20 hours. The desired product may be obtained by standard techniques, for example by column chromatography or, preferably, by distillation.

It is believed that, in the process, the first step is the oxidation of the or each —$CH_2$— group in the compound of general formula II by oxygen in conjunction with the fluorinating system which may act catalytically. In the oxidation reaction, the fluorinating system may deprotonate the or each —$CH_2$— group to produce a carbanion or at least activate the or each —$CH_2$— group, which then reacts with oxygen to produce a ketone group. Water may also be produced in the reaction. In order to aid the reaction, a means for removing water formed may be included.

It is believed that the diphenylketone derivative formed in the first step is important for the stabilisation of intermediates formed in the second step which may comprise the nucleophilic substitution of the group $L^1$ and/or group $L^2$.

Nucleophilic substitution of group $L^1$ and/or $L^2$ preferably involves substitution by fluoride ions provided by said fluorinating system to produce a compound of general formula I wherein Y and Z represent fluorine atoms. Such a compound can advantageously be used directly in the production of polyketones for example polyetheretherketone (PEEK) when n and m represent 0.

Compounds of general formula I wherein at least one of the substituents Y and Z represents a hydroxy group may involve nucleonphilic substitution of group $L^1$ and/or group $L^2$ by hydroxide ions from water generated in the oxidation of the or each —$CH_2$— group as described above or, alternatively, may involve nucleophilic substitution by hydroxide ions of a compound of general formula I wherein substituent Y and/or Z represent fluorine atoms.

In some circumstances, the group $L^1$ and/or the group $L^2$ of the compound of general formula II may be oxidised prior to undergoing a nucleophilic substitution reaction. Such an oxidation reaction may be achieved by said fluorinating system in the presence of oxygen or by addition of another oxidising agent. For example, where $L^1$ and/or $L^2$ represent an amine group in said compound of general formula II, the or each amine group may be oxidised, initially, to a nitro group, which can then undergo a nucleophilic substitution reaction with fluorine or hydroxide ions, as described above. Alternatively, an amino group may be converted to a leaving group, for example a group —$NH_3^+$, which may be substituted.

Nucleophilic substitution of compounds of general formula II wherein group $L^1$ and/or $L^2$ represent nitro groups result in the displacement of nitrite ions. The substitution reaction may, therefore, be aided by providing a nitrite trap to remove the nitrite ions. Phthaloyl dichloride may be added to the reaction mixture to act as a nitrite trap.

As described above, group $L^1$ and group $L^2$ are preferably nitro groups in said compound of general formula II. Such a nitro compound can be prepared from a compound of general formula II wherein $L^1$ and $L^2$ represent amine groups, by oxidation using hydrogen peroxide. Such an amine compound of general formula II is commercially available and/or can be prepared using standard procedures from commercially available reagents.

As described herein, it has been found, surprisingly, that fluorinating systems which comprise an organics soluble fluoride source can be used to oxidise certain diphenylmethanes to diphenylketones in the presence of oxygen. Accordingly, the invention extends to a process for the preparation of a compound of general formula I as described above wherein Y and Z each independently represent a halogen atom or a hydroxy, nitro or amino group, which includes the step of contacting a compound of general formula II as described above, wherein $L^1$ and $L^2$ each independently represent a halogen atom or a hydroxy, nitro or amino group, with an organics soluble fluoride source in the presence of oxygen.

The organics soluble fluoride source may be as described in any statement herein.

Preferably, said organics soluble fluoride source acts as a catalyst in the oxidation reaction.

Oxygen may be supplied in the process as described in any statement herein.

A preferred halogen atom is a fluorine atom.

Preferably, Y, Z, $L^1$ and $L^2$ independently represent a fluorine atom or a hydroxy group. Preferably, Y and $L^1$ and/or Z and $L^2$ represent the same atom or group.

The process may include a solvent as described in any statement herein.

The invention extends to a compound of general formula I prepared in a process as described herein.

Any feature of any aspect of an invention described herein may be combined with any feature of any other aspect described herein.

The invention will now be described, by way of example.

EXAMPLE 1

Tetramethylammonium fluoride tetrahydrate (0.097 g, 6 mmol) in dimethylsulphoxide (10 ml) was azeotropically dried, for 2.5 hours with efficient stirring, using cyclohexane (40 ml) under an argon atmosphere. The argon atmosphere was then removed and replaced with an air feed. The temperature was increased to 100° C. and 4,4'-dinitrodiphenylmethane (0.05 g, 2 mmol) added. The reaction was monitored using gas chromatography (GC). Initially, the reaction mixture went blue but, after 20 minutes, the mixture went brown and 4,4'-difluorobenzophenone was visible in the GC trace. After 1 hour, no starting material was visible in the GC trace; the major product visible was 4,4'-difluorobenzophenone (75%), with minor products being 4-fluoro-4'-nitrobenzophenone, 4-fluoro-4'-hydroxybenzophenone and 4,4'-dinitrobenzophenone. After 24 hours, gas chromatography-mass spectrometry (GC-MS) showed that 100% conversion of 4,4'-dinitrodiphenylmethane had been achieved, with 84% conversion to 4,4'-difluorobenzophenone, 10% conversion to 4-fluoro-4'-hydroxybenzophenone and traces of other compounds being observed.

EXAMPLE 2

Tetramethylammonium fluoride tetrahydrate (TMAF) was dried under a dynamic vacuum at 60° C. until a hygroscopic white solid was obtained (19.4% water w/w by Karl Fischer titration). N,N-Dimethylacetamide was dried over 3 Å and 4 Å molecular sieves for at least three days before use. 4,4'-Dinitrodiphenylmethane (0.062 g, 0.24 mmol) was placed in a three-necked, 100 ml round bottomed flask along with biphenyl (0.03 g, 0.2 mmol), the internal standard. N,N-Dimethylacetamide (10 ml) was added along with an oxygen feed. The solution was heated to 100° C. with stirring. After 20 minutes of oxygen bubbling through the system, TMAF (0,086 g, 0.7 mmol) was added. The reaction was monitored by gas chromatography (GC). Initially, the reaction went blue, but gradually turned red over 15 minutes. During the course of the reaction, starting material, 4-fluoro-4'-nitrobenzophenone and 4,4'-difluorobenzophenone could be detected by GC. After 1 hour, no starting material was visible in the GC trace; the only detectable product was 4,4'-difluorobenzophenone (48%)

EXAMPLE 3

TMAF and N,N-dimethylacetamide were pre-dried as described in Example 2. 4,4'-Dinitrodiphenylmethane (0.062 g, 0.24 mmol) was placed in a 100 ml, three-necked round bottomed flask with an oxygen feed, along with biphenyl (0.03 g, 0.2 mmol), the internal standard. Keeping the flask at ambient temperature, TMAF (0.005 g, 0.04 mmol) was added, resulting in immediate blue colouration of the solution. After stirring overnight, the solution had become red with GC and $^1$H-nmr analysis demonstrating that quantitative conversion to 4,4'dinitrobenzophenone had occurred. The solution was then heated to 100° C. and a further quantity of TMAF (0.086 g, 0.7 mmol) added. 4,4'-Dinitrobenzophenone, 4-fluoro-4'-nitrobenzophenone and 4,4,'-difluorobenzophenone could be detected in the GC trace during the reaction, but after 1 hour, GC showed that 100% conversion of 4,4'-dinitrobenzophenone had been achieved, with the only detectable product being 4,4'-difluorobenzophenone (71%).

EXAMPLE 4

TMAF was dried as described in Example 2. Sulfolane was distilled from sodium hydroxide into a flask and kept over 3 Å and 4 Å molecular sieves. 4,4'-Dinitrodiphenylmethane (0.062 g, 0.24 mmol) was added to a 100 ml round bottomed flask with an air feed, along with biphenyl (0.03 g, 0.2 mmol), the internal standard. TMAF (0.008 g, 0.07 mmol) was added along with sulfolane (10 ml), giving an immediate blue colouration. After stirring overnight, the solution had become red. This solution was heated to 100° C. and a further quantity of TMAF (0.086 g, 0.7 mmol) added. 4,4'-Dinitrobenzophenone, 4-nitro-4'-fluorobenzophenone and 4,4'-difluorobenzophenone could be detected in the GC trace during the reaction. After two hours, GC showed that 100% conversion of 4,4'-dinitrobenzophenone had been achieved, with the only detectable product being 4,4'-difluorobenzophenone (70%).

EXAMPLE 5

Tetramethylammonium hydrogen difluoride (TMAHF$_2$) was dried under a dynamic vacuum at 60° C. overnight to give a free-flowing white solid. N,N-Dimethylacetamide was dried as described in Example 2. 4,4'-Dinitrodiphenylmethane (0.069 g, 0.27 mmol) was placed in a 100 ml round bottomed flask with an oxygen feed, along with biphenyl (0.03 g, 0.2 mmol), the internal standard. Keeping the flask at ambient temperature, TMAHF, (0.0166, 0.015 mmol) was added, which slowly turned the mixture blue. After stirring overnight, the solution had become red. The solution was heated to 140° C. and a further quantity of TMAHF$_2$ (0.1841, 1.6 mmol) added. During the reaction, 4,4'-dinitrobenzophenone, 4-fluoro-4'-nitrobenzophenone and 4,4'-difluorobenzophenone could be detected in the GC trace. After 4 hours, GC showed only the presence of 4-nitro-4'-fluorobenzophenone (6% ) and 4,4'-difluorobenzophenone (71%).

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. A process for the preparation of a compound of general formula

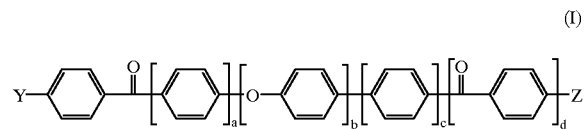

(I)

wherein Y and Z each independently represent a fluorine atom or a hydroxy group, and a, b, c and d independently represent 0, 1, 2 or 3 provided that the sum of a, b, c and d is 1, 2, 3 or 4, the process comprising treating a compound of general formula

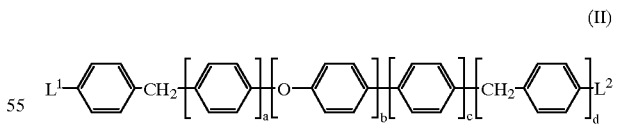

(II)

wherein a, b, c and d are as described above and $L^1$ and $L^2$ each independently represent a leaving group or a group which is oxidisable to a leaving group provided that either Y and $L^1$ are different or Z and $L^2$ are different, with a fluorinating system in the presence of oxygen.

2. A process according to claim 1, wherein $L^1$ and $L^2$ independently represent a halogen atom or a nitro or amino group.

3. A process according to claim 1, wherein $L^1$ and $L^2$ represent the same atom or group.

4. A process according to claim 1, wherein a represents 0 or 1, b represents 0, 1 or 2, c represents 0 or 1 and d represents 0 or 1.

5. A process according to any preceding claim wherein said fluorinating system is involved in both the oxidation of the —$CH_2$— groups and in the reaction of the group $L^1$ and/or group $L^2$.

6. A process according to claim 1, wherein said fluorinating system includes an organics soluble fluoride source.

7. A process according to claim 1, wherein said fluorinating system includes an onium fluoride derivative.

8. A process according to claim 1, wherein said fluorinating system is selected from ammonium, phosphonium and sulphonium fluoride derivatives.

9. A process according to claim 1, wherein said process is carried out in the presence of an aprotic solvent.

10. A process according to claim 1, wherein at least one or Y and z represent a fluorine atom.

11. A process according to claim 1, wherein both of Y and Z represent a fluorine atom.

* * * * *